US00PP29232P3

(12) United States Plant Patent
Probst

(10) Patent No.: US PP29,232 P3
(45) Date of Patent: Apr. 10, 2018

(54) ***COREOPSIS* PLANT NAMED 'PROORY'**

(50) Latin Name: *Coreopsis hybrida*
Varietal Denomination: Proory

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 14/998,334

(22) Filed: Dec. 31, 2015

(65) Prior Publication Data

US 2017/0196158 P1 Jul. 6, 2017

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

PUBLICATIONS

Moerheim New Plant introduces unprecedented flowered *Coreopsis*"KA-POW" on Plantarium 2015, retrieved on Apr. 10, 2017, retrieved from the Internet at <http://elbee.prco/108241-moerheim-new-plant-introduceert-ongekend-grootbloemige-coreopsis-ka-pow-op-plantarium-2015> 2 pp.*

Google English translation of Moerheim New Plant, retrieved on Apr. 10, 2017, 2 pp.*

Star Roses & Plants Conard-Pyle 2016 Breakthrough Breeding Innovative Introductions, retrieved on Apr. 10, 2017, retrieved from the Internet at <https://issuu.com/starrosesandplants/docs/2016_catalog/18> p. 14.*

* cited by examiner

*Primary Examiner* — June Hwu

(74) *Attorney, Agent, or Firm* — Buchanan Ingersoll & Rooney PC

(57) ABSTRACT

The present *Coreopsis* variety was created during a controlled plant breeding program. A vigorous, compact and bushy growth habit is displayed. Attractive, large cream-colored flowers are displayed with the ray florets having a burgundy red eye zone and burgundy red suffusion throughout the ray florets during cooler growing conditions. The green foliage coloration contrasts nicely with the lighter blossom coloration. Excellent resistance to powdery mildew has been displayed during observations to date. The plant is a perennial and has been observed to be hardy to at least U.S.D.A. Hardiness Zone No. 5. The plant can be grown to advantage as attractive ornamentation in parks, gardens, and residential settings.

1 Drawing Sheet

Botanical/commercial classification: *Coreopsis hybrida*/Tickseed Plant.

Varietal denomination: cv. Proory.

SUMMARY OF THE INVENTION

Plants of *Coreopsis* sometimes bear a common name such as Tickseed, and are recognized to be ornamental herbaceous plants for landscape or container uses.

The new variety of *Coreopsis* hybrid was created from an ongoing controlled breeding program in 2010 in Hubbardston, Mass., U.S.A. The objective of the breeding program was to develop new varieties having superior attributes that are long-lived, exhibit a perennial habit to at least U.S.D.A. Hardiness Zone No. 5, and display an array of attractive flower colorations and plant forms. The female parent (i.e., the seed parent) of the new variety was an unnamed, unreleased, and non-patented *Coreopsis* plant designed Q2 09-7. Pollen used for the cross was pooled from a mixture of unnamed, unreleased, and non-patented *Coreopsis* plants that displayed limited fertility with the formation of a limited quantity of pollen. The exact male parent that contributed to the origin of the new variety is unknown.

It was found that the new *Coreopsis* plant displays the following combination of characteristics:

(a) displays a compact and bushy growth habit,
(b) displays attractive large cream-colored flowers with the ray florets exhibiting a burgundy red eye zone and burgundy red suffusion throughout the ray florets during cooler growing conditions,
(c) exhibits excellent resistance to powdery mildew, and
(d) is hardy to at least U.S.D.A. Hardiness Zone No. 5.

When compared to the 'Promon' cultivar (U.S. Plant patent application Ser. No. 14,757,512, filed Dec. 23, 2015) a different coloration of the ray florets is observed. More specifically, the ray florets of the new cultivar are of a lighter cream coloration and those of the 'Promon' cultivar are bright yellow. The eye zone of the ray florets of the new cultivar is burgundy red regardless of temperature and the eye zone of the ray florets of 'Promon' cultivar is burgundy red during cooler growing conditions. Also, the ray florets of the new cultivar tend to assume a burgundy red suffusion throughout during cooler growing conditions.

The new cultivar also can be readily distinguished from the 'Star Cluster' cultivar (U.S. Plant Pat. No. 23,035). More specifically, the new cultivar displays a more compact and sturdier growth habit.

The expressed combination of characteristics also enables the new cultivar to be readily distinguished from the 'Full Moon' variety (U.S. Plant Pat. No. 19,364) which forms large clear yellow flowers. Unlike the 'Full Moon' variety, the new variety displays ray florets having a lighter cream coloration with a burgundy eye zone, a more compact growth habit, and a better resistance to powdery mildew.

Additionally, the new variety can be readily distinguished from its ancestors. More specifically, the female parent (i.e., the seed parent), *Coreopsis* plant designed Q2 09-7 displays white flowers with a rose-purple edge and no eye, and is very fertile producing an abundance of seeds, whereas the new variety displays cream-white with a burgundy red eye colored flowers and is sterile.

The new variety can be grown in the ground or in a container to provide attractive ornamentation in parks, gardens, and residential settings.

Asexual reproduction of the new variety in a controlled environment by the rooting of vegetative cuttings, such as stem cuttings (e.g., terminal tip cuttings), has been conducted at West Grove, Pa., U.S.A. It has been demonstrated that the combination of characteristics of the new cultivar is firmly fixed and is well retained in succeeding generations. Accordingly, the new cultivar can be asexually reproduced in a true-to-type manner. The new variety also can be asexually propagated by division.

The new cultivar has been named 'Proory'.

BRIEF DESCRIPTION OF THE PHOTOGRAPH

The accompanying photograph illustrates a typical flowering plant of the new cultivar at an age of approximately two years. The plant had been asexually reproduced by the use of vegetative cuttings, such as stem cuttings (e.g., terminal tip cuttings), and was growing outdoors on its own roots during June 2014 at West Grove, Pa., U.S.A. The attractive large cream-colored ray florets having a burgundy red eye zone combined with a compact and bushy growth habit are shown.

DETAILED BOTANICAL DESCRIPTION

The chart used in the identification of the colors described herein is The R.H.S. Colour Chart of The Royal Horticultural Society, London, England (1995 Edition). The plant had been asexually reproduced by the rooting of vegetative cuttings, such as stem cuttings (e.g., terminal tip cuttings), was approximately one year of age, and was observed during June while growing in a container at West Grove, Pa., U.S.A.

Botanical classification: *Coreopsis hybrida.*

Cultivar: Proory.

Plant:

- *Habit.*—Vigorous herbaceous perennial, compact and bushy, clump-forming with study stems and an upright and spreading canopy.
- *Height.*—Approximately 45 to 50 cm on average. This compares to approximately 30 to 45 cm on average for the 'Promon' cultivar, approximately 65 cm on average for the 'Star Cluster' cultivar, and approximately 70 to 75 cm on average for the 'Full Moon' cultivar.
- *Width.*—Approximately 45 to 50 cm on average. This compares to approximately 100 cm on average for the 'Full Moon' cultivar.
- *Branching.*—Highly branched, commonly with approximately 10 basal branches on average and approximately 3 to 5 secondary branches on average.
- *Branch internodes.*—Arise opposite at nodes, variable, and typically approximately 4 cm in length.
- *Stem shape.*—Substantially round and wiry.
- *Stem length.*—Main stems commonly are approximately 18 cm in length on average with laterals of approximately 8 cm in length (excluding peduncles).
- *Stem diameter.*—Main stems commonly are approximately 4 mm in diameter on average.
- *Stem texture.*—Glabrous.
- *Stem color.*—Near Green Group 137A.
- *Roots.*—Fibrous, fine, and well branched.

Foliage:

- *Arrangement.*—Opposite, single, sessile.
- *Configuration.*—Simple with trifid upper leaves, lanceolate with lanceolate secondary lobes.
- *Length.*—Variable, up to approximately 10 cm in length for entire leaves, secondary lobes commonly average approximately 5 cm in length on average.
- *Width.*—Variable, and up to 1.2 cm in width for entire leaves, and up to approximately 5 cm in width for trifid leaves, secondary lobes commonly average approximately 6 mm in width on average.
- *Apex.*—Narrowly acute.
- *Base.*—Attenuate.
- *Margin.*—Entire with short pubescence and slight undulations.
- *Texture.*—Glabrous.
- *Color.*—Young leaves: near Yellow-Green Group 144A on the upper surface, and near Yellow-Green Group 144B on the under surface. Mature leaves: near Green Group 137A on the upper surface, and near Green Group 137B on the under surface.

Flower description:

- *Quantity.*—When grown in a one-gallon container commonly 120 flowers are displayed at a time, with an average of approximately 6 per lateral branch.
- *Bud shape.*—Generally spherical.
- *Bud size.*—Approximately 8 mm in length and diameter on average.
- *Bud color.*—Yellow Group 2A, and covered with bracts of Yellow-Green Group 146C.
- *Flower appearance.*—Large daisy-type composite inflorescence form with elongated oblong-shaped ray florets and disc florets at the center forming a radiant head. Inflorescences are borne on terminals arising from leaf axils.
- *Lastingness.*—Commonly approximately one week until senescence of ray florets while disc florets and bracts tend to be persistent.
- *Flowering response.*—Under normal conditions, plants flower from June to August in southeastern Pennsylvania, U.S.A.
- *Inflorescence diameter.*—Commonly up to about 6.5 cm on average when fully open.
- *Inflorescence depth.*—Commonly up to approximately 1.2 cm on average when open.
- *Disc.*—Commonly up to approximately 1 cm in diameter on average.
- *Fragrance.*—Slightly acrid when crushed.
- *Ray florets.*—Aspect: commonly in three longitudinal sections with the central section being the longest. Shape: generally oblong. Length: approximately 2.8 cm on average. Width: approximately 1.5 cm on average. Apex: emarginated with three notches. Base: broadly cuneate. Margin: entire with notched apex. Texture: glabrous on both surfaces. Number: approximately eight arranged in a single whorl.

Color: on the upper surface when opening and when mature near Yellow Group 2C at the tip, transitioning to near Green-Yellow Group 2A, and with an eye spot of near Red Group 46A at the base, and on the under surface when opening and when mature commonly with a blend near Green-Yellow Group 2A, 2B, and 2C. During cooler growing conditions the upper surface commonly is suffused with Red Group 46A. During the summer, warmer growing conditions the upper surface commonly is sporadic suffusion with reddish coloration.

*Disc florets*.—Arrangement: massed at the center of the inflorescence. Shape: tubular, fused at the base, and flared at the apex. Length: commonly approximately 7 mm on average. Width: commonly approximately 1 mm on average at the base. Color: primarily near Greyed-Orange Group 163B when immature, near Yellow Group 5C when fully open, becoming Greyed-Orange Group 165B when dried as the ray florets drop. The base is near Yellow Group 5C with a flared portion of near Yellow Group 5A.

*Reproductive organs*.—Location: androecium and gynoecium present only among disc florets. Stamen number: five per floret fused into a tube surrounding the style. Anther size: approximately 3 mm in length on average and approximately 0.4 mm in width on average. Anther color: near Greyed-Orange Group 165B. Pollen quantity: moderately produced during observations to date. Pistil number: one per floret. Pistil length: approximately 6 mm on average. Style appearance: very fine. Style color: near Yellow-Green Group 154D and somewhat translucent. Stigma shape: bifid and pilose, with recurved branches approximately 1 mm in length. Stigma color: commonly near Yellow-Orange Group 17A. Ovary size: commonly approximately 1.5 mm in length on average, and approximately 1 mm in width on average. Ovary color: near Yellow-Green Group 154D. Receptacle size: approximately 4 mm in diameter on average and approximately 2 mm in depth on average. Receptacle color: near Yellow-Green Group 144D. Seeds/fruit: none encountered during observation to date.

*Involucral bracts*.—Number: commonly in two rows of eight. Arrangement: the outer bracts are unfused and somewhat reflexed when the flower is fully open and becoming substantially horizontal after the ray florets drop. The inner bracts overlap and surround the receptacle in a campanulate form with the apical portion unfused and spreading and held close to the ray florets. Shape: the outer bracts are lanceolate, and the free portions of the inner bracts are lanceolate. Size: outer bracts commonly up to approximately 7 mm in length and approximately 2 mm in width at the widest point, and inner bracts approximately 1 cm in length and approximately 6 mm in width with a free portion approximately 5 mm in length and approximately 4 mm in width. Apex: narrowly acute for the outer bracts and apiculate for the inner bracts. Texture: somewhat waxy on the inner bracts and the outer bracts are puberulent. Bases: truncate. Color: outer bracts are near Green Group 138A on both surfaces, the fused portion of the inner bracts is near Yellow-Green Group 147B, the unfused portion of the inner bracts is near Yellow-Green Group 147B on both surfaces, and the center, apex and margin are near Yellow-Green Group 152B.

*Peduncles*.—Strength: relatively strong. Size: commonly approximately 8 cm in length on average, and approximately 1.5 mm in diameter on average. Texture: glabrous. Color: commonly near Green Group 137A.

Disease resistance: Excellent with respect to powdery mildew, such as *Sphaerotheca macularis*, during observations to date. This resistance has been observed to exceed that commonly displayed by other large-flowered *Coreopsis grandiflora* plants grown under the same conditions.

Hardiness: Hardy to at least U.S.D.A. Hardiness Zone No. 5 during observations to date.

Propagation: Through the rooting of vegetative cuttings, including stem cuttings (e.g., terminal tip cuttings), or by division.

Plants of the new 'Proory' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Coreopsis* plant having the following combination of characteristics:

(a) displays a compact and bushy growth habit, (b) displays attractive large cream-colored flowers with the ray florets exhibiting a burgundy red eye zone and burgundy red suffusion throughout the ray florets during cooler growing conditions, (c) exhibits excellent resistance to powdery mildew, and (d) is hardy to at least U.S.D.A. Hardiness Zone No. 5;

substantially as illustrated and described.

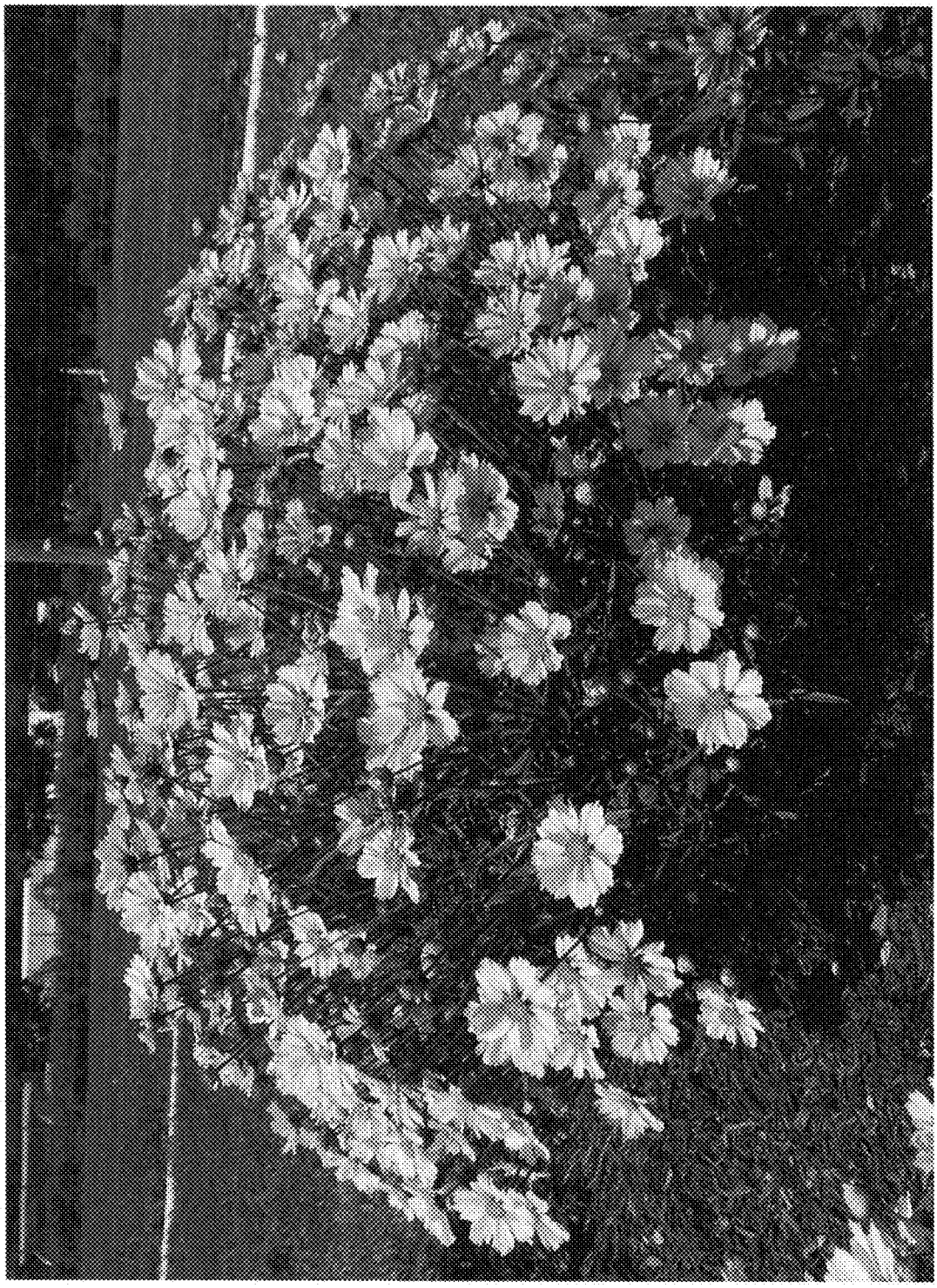

* * * * *